(12) United States Patent
Early et al.

(10) Patent No.: US 6,197,271 B1
(45) Date of Patent: Mar. 6, 2001

(54) CATALYTIC REACTOR AND PROCESS FOR EXOTHERMIC GAS PHASE REACTIONS

(75) Inventors: Simon Robert Early, London; George Edwin Harrison, Billericay; John Wilson Kippax, Richmond, all of (GB)

(73) Assignee: Kvaerner Process Technology Limited, London (GB)

( * ) Notice: Subject to any disclaimer, the term of this patent is extended or adjusted under 35 U.S.C. 154(b) by 0 days.

(21) Appl. No.: 09/101,047
(22) PCT Filed: Dec. 23, 1996
(86) PCT No.: PCT/GB96/03234
 § 371 Date: Dec. 10, 1998
 § 102(e) Date: Dec. 10, 1998
(87) PCT Pub. No.: WO97/24175
 PCT Pub. Date: Jul. 10, 1997

(30) Foreign Application Priority Data

Dec. 29, 1995 (GB) .................................................. 9526674

(51) Int. Cl.⁷ ............................. C01C 1/04; C07C 27/00; B01J 10/00; B01J 8/04; B01J 35/02
(52) U.S. Cl. .................. 423/359; 423/361; 422/187; 422/191; 422/193; 422/195; 422/211; 518/700; 518/713
(58) Field of Search ................. 422/191, 187, 422/193, 195, 211; 423/359, 361; 518/700, 713

(56) References Cited

U.S. PATENT DOCUMENTS

| 4,087,252 | 5/1978 | Strahorn et al. | 23/288 R |
|---|---|---|---|
| 4,578,248 | 3/1986 | Nagaoka | 422/310 |
| 5,756,048 | * 5/1998 | Zardi et al. | 422/49 |

FOREIGN PATENT DOCUMENTS

| 0 026 057 | 4/1981 | (EP) | B01J/8/04 |
|---|---|---|---|
| 0 075 056 A1 | 3/1983 | (EP) . | |
| 0 248 284 | 12/1987 | (EP) | B01J/8/04 |
| 2 065 492 | 7/1981 | (GB) . | |
| 065462 | * 7/1981 | (GB) . | |
| WO 95/03867 | 2/1995 | (WO) . | |

* cited by examiner

*Primary Examiner*—Steven P. Griffin
*Assistant Examiner*—Maribel Medina
(74) *Attorney, Agent, or Firm*—Senniger, Powers, Leavitt & Roedel

(57) ABSTRACT

Disclosed is a reactor and process for exothermic vapour phase reaction, wherein the reactor (1; 101) comprises a pressure vessel (2; 102) having an inlet (3;103) for reactant (s) and an outlet (4; 104) for products; a plurality of beds (5; 105) with heterogeneous catalyst, each bed supported by a catalyst support grating (6; 106); a vapour collection chamber (9; 109) and a vapour redistribution chamber (10; 110) between successive pair(s) of beds for redistribution of vapourous reaction mixture over the inlet of the next bed; a diaphragm (11; 111) separating the vapour collection chamber (9; 109) from the vapour redistribution chamber; at least one pair of nested trough members extending at least partially across the diaphragm, each comprising an inner trough member (14; 114) having one or more apertures (18; 118), an outer trough (20; 120) having one or more apertures (21; 121) and a quench gas conduit (15; 115) provided with apertures (17; 117); the apertures (18; 118; 21; 121; 17; 117) arranged to provide a tortuous pathway for the flow of vapour and quench gas.

23 Claims, 10 Drawing Sheets

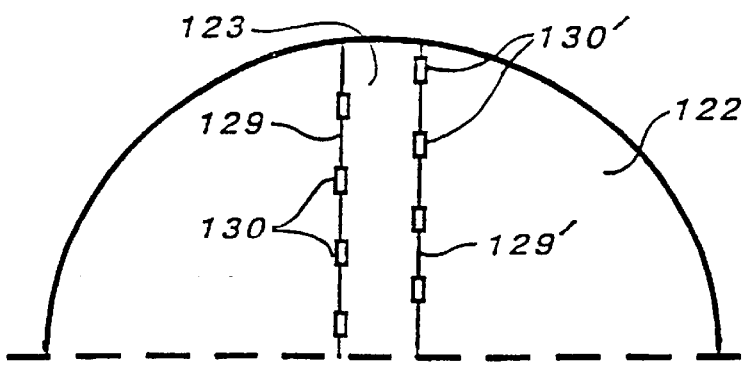
FIG. 13
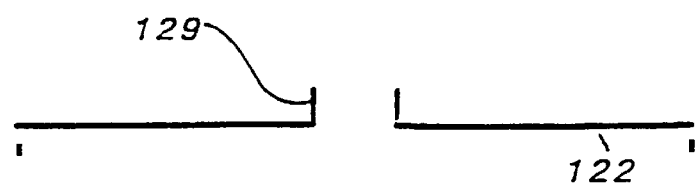
FIG. 13a
FIG. 13b
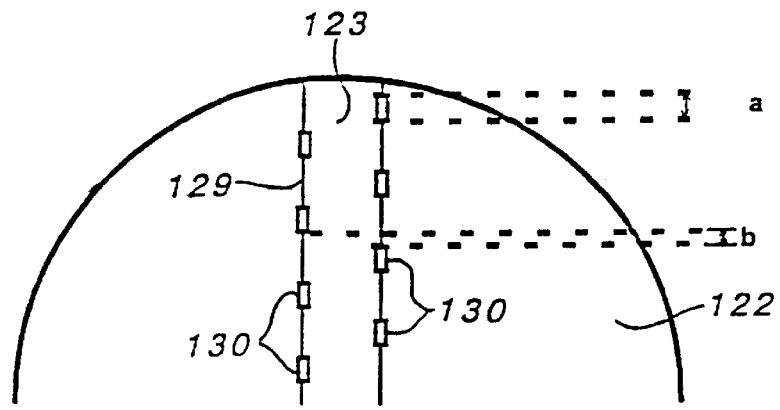
FIG. 14
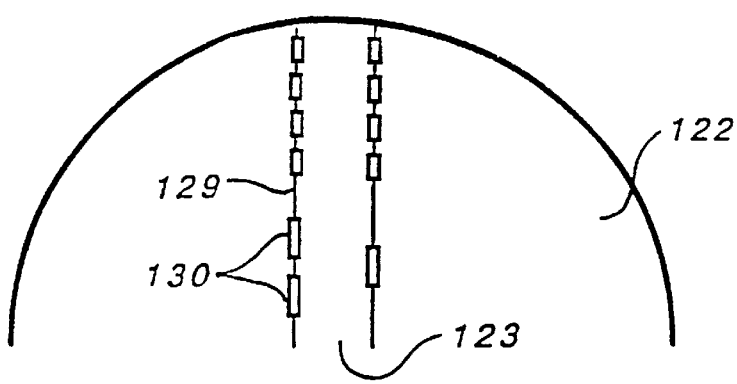
FIG. 15

CATALYTIC REACTOR AND PROCESS FOR EXOTHERMIC GAS PHASE REACTIONS

The present invention relates to a chemical reactor for use in equilibrium limited exothermic gas phase reactions, such as methanol synthesis or ammonia synthesis and to a process for conducting exothermic vapour phase reactions.

The evolution of ammonia and methanol reactors from the 1960s to the 1980s is outlined in a paper entitled "Review these developments in ammonia and methanol reactors" by Umberto Zardi which was published in the August 1982 edition of *"Hydrocarbon Processing"* at pages 129ff. The first reactor described in this paper is the single bed Ammonia Casale axial reactor, designed for ammonia production, in which the synthesis gas flows under high pressure and temperature axially through a single catalyst bed mounted in a cylindrical reactor. Subsequent developments include the introduction of multi-bed designs and reactors utilising radial as well as axial flow through the beds.

Thus, EP-A-0026057 describes an integrated process for the production of ammonia or methanol in which an appropriate synthesis gas is passed through a series of catalyst beds and, between each bed, the gas is quenched, by the injection of quench gas between the beds. Quenching the reaction mixture between catalyst beds helps to shift the equilibrium of the exothermic gas phase reaction(s) in a favourable direction and to alleviate the undesirable effects of the presence of pockets of vapour of elevated or reduced temperature. These effects include, in the case of hot pockets, deterioration of catalyst and, in the case of cold pockets, possible snuffing of the reaction. Similarly, EP-A-0248284 relates to a reactor for use in the production of ammonia, in which the reactor comprises a number of catalyst beds wherein cooler quench gas is supplied to the reactor between each bed. The purpose of this quench gas is the same as in EP-A-0026057, i.e. to shift the equilibrium of the exothermic gas phase reaction(s) in a favourable direction and to alleviate the undesirable effects of non-uniform temperature distribution within the catalyst beds.

The efforts of the prior art to counteract the problem of temperature inhomogeneity in catalyst beds during equilibrium limited exothermic gas phase reactions have not been entirely successful and there is a need in the art for a reactor design which will yield increased catalyst life and performance.

According to the present invention there is provided a reactor for conducting an exothermic vapour phase reaction comprising:

a) a pressure vessel having inlet means for supply of a gaseous reactant or reactants and outlet means for recovery of a product-containing stream therefrom;

b) a plurality of beds of a heterogeneous catalyst effective for catalysis of the exothermic vapour phase reaction in the path of a material passing from the inlet means to the outlet means, each bed being supported within the pressure vessel by a respective support means;

c) a vapour collection chamber and a vapour redistribution chamber between the or each successive pair of beds, the vapour collection chamber being arranged to collect a vaporous reaction mixture from an exit end of one bed of the pair and the vapour redistribution chamber being arranged to redistribute vapour over the inlet end of the other bed of the pair;

d) a diaphragm extending across the interior of the pressure vessel and separating the vapour collection chamber from the vapour redistribution chamber;

e) at least one pair of nested trough members, the or each pair comprising an inner trough member and an outer trough member associated with the diaphragm and extending at least partially thereacross, the inner trough member and the outer trough member being nested so as to define a space therebetween, the inner trough member opening to the vapour collection chamber and having one or more first apertures along its length and the outer trough member communicating laterally on each side with the vapour redistribution chamber by means of one or more second apertures opening laterally of the outer trough member along a respective side thereof, the space between the inner trough member and the outer trough member providing a tortuous passageway for vapour from the vapour collection chamber to the vapour redistribution chamber through the at least one first aperture, through the space between the inner trough member and the outer trough member, and then through the at least one second aperture to discharge laterally into the vapour redistribution chamber; and f) a quench gas conduit associtated with the or each pair of trough members and being provided with one or more third apertures along its length arranged to discharge quench gas into the vapour flowing along the tortuous pathway.

The pressure vessel may be of any size and shape but is preferably circular in cross-section. Preferably the inlet means and the outlet means are axially spaced one from another so that the overall direction of flow of reactants and products is from one end portion of the reactor to the other.

In one arrangement the beds of catalyst are substantially cylindrical.

The trough members may be of any suitable section provided that lateral discharge of vapour into the vapour redistribution chamber is possible. A preferred form of trough member is arcuate in section. Preferably the angle subtended by the arc of an arcuate section trough member is from about 120° up to about 180°. Semi-circular section trough members may be used. Alternatively the trough members may be part-elliptical, for example, semi-elliptical in section. If desired, the trough members may be formed with one or more planar faces. For example, it is envisaged that a trough member with a flat bottom and arcuate sides could be used, or a trough member with a flat bottom and inclined planar sides, which may be inclined, usually outwardly inclined to the bottom of the trough member. The angle of inclination between the sides and the bottom of the trough may be any suitable angle, for example from about 30° to about 90°.

In one preferred arrangement the quench gas conduit associated with the or each respective pair of trough members is mounted at least partially within the inner trough member of the pair.

The first and second apertures in the inner and outer trough members respectively may be of any suitable shape, e.g., circular, elliptical or rectangular, as may also be the third aperture or apertures in the quench gas conduit. The inner and/or outer trough members may each have only a single first or second aperture respectively, the aperture being provided in the form of an elongate slot. However, it will normally be preferred for ease of construction to provide a plurality of apertures along the length of the respective trough member. Similarly, although the quench gas conduit may have a single elongate slot to serve as the third aperture, it will normally be preferred to provide a plurality of third apertures along the length of the conduit for ease of construction and to enable the quench gas conduit to retain sufficient structural strength.

When the diaphragm and associated nested trough members are the only means of vapour redistribution provided between successive catalyst beds of the reactor it is preferred that the position of the second apertures be arranged such that the radial displacement, with respect to the nearest point on a reference axis lying in the plane of the diaphragm and also in a perpendicular plane bisecting the outer trough member along its longitudinal axis, of the second apertures from the plane of the diaphragm is not more than about 45°. However, this angle may be greater than 45° when further means of vapour redistribution are provided between catalyst beds, as will be explained further below.

The second apparatus may be arranged in one or more rows on each side of the outer trough member so that the discharge of quenched reaction mixture to the vapour redistribution chamber is through a set of one or more rows of second apertures on one side of the outer trough member and through a corresponding set of one or more rows of second apertures on the other side thereof.

The reactor includes one or more quench gas conduits for supply of quench gas which desirably segment the diaphragm in a symmetrical arrangement.

In a preferred arrangement the third aperture or apertures of the quench gas conduit is or are aligned with the first aperture or apertures of the inner trough member. In this way the stream of quench gas from the conduit serves to draw vapour from the vapour collection chamber into the space between the inner and outer trough members by means of an eductive effect created by the stream of quench gas issuing from the third aperture or apertures of the quench gas conduit. In this way the quench gas and entrained vapour are turbulently mixed in passage along the tortuous pathway before passing on through the second apertures into the vapour redistribution chamber.

As mentioned above, the quench gas conduit or conduits preferably segment or partially segment the diaphragm in a symmetrical arrangement. Hence, if there is only one quench gas conduit this will normally extend substantially diametrically at least partially across the pressure vessel. If there are two or more quench gas conduits, then these may extend at least partially along chords across the pressure vessel; in this way substantially uniform mixing of the quench gas with the vapour flowing through the diaphragm and substantially uniform redistribution in the vapour redistribution chamber can be achieved.

Although the corresponding quench gas conduits of different diaphragms can lie in common planes parallel to or including the axis of the pressure vessel, it is also envisaged that any given diaphragm may be radially offset about the axis of the pressure vessel relative to an adjacent diaphragm so that the quench gas conduit or conduits of one diaphragm is or are radially offset about the axis of the reactor with respect to the corresponding conduit or conduits of at least one other diaphragm within the pressure vessel. Thus the angle of radial displacement about the axis of the pressure vessel of the quench gas conduits of one diaphragm relative to an adjacent diaphragm may range from about 20° to about 90°, e.g. about 45° or about 60°. A preferred angle is 90°. Any practical number of catalyst beds may be employed in the reactor of the invention. Preferably three or more beds are used. Moreover, there is no limit to the number of diaphragms or to the angle of offsetting about the axis of the pressure vessel of the quench gas conduit or conduits of one diaphragm relative to that or those of an adjacent diaphragm which may be envisaged.

In one embodiment of the invention, five catalyst beds are employed, with four diaphragms therebetween. However, it is also possible using the teachings of the invention to have two, three, four, six, seven, eight, nine or more catalyst beds in the reactor.

The radial offsetting of the quench gas conduits, and hence of the associated trough members, of adjacent diaphragms is an important preferred feature of the invention because it helps to ensure that temperature inhomogeneity across the cross-section of each catalyst bed is kept to a minimum. Thus, if after passage through a diaphragm, a localised pocket of hot gas were present, this pocket would then increase in temperature even further relative to the whole stream on passage through a subsequent catalyst bed. If the quench gas conduits and trough member of successive diaphragms are aligned this increases the possibility that a local pocket of hot gas will prevail from one catalyst bed to the next and so on until the outlet of the reactor is reached, causing premature deterioration of the catalyst and inefficient utilisation thereof. Respective radial offsetting of successive diaphragms decreases the likelihood of this occurring. Similarly, a localised pocket of cold gas in a catalyst bed, which could cause snuffing of the reaction if allowed to prevail in a subsequent catalyst bed of the reactor, is less likely to persist as a result of this preferred feature of the invention.

The catalyst for use in methanol synthesis is preferably selected from but is not limited to copper-containing catalysts, for example reduced CuO-ZnO catalysts. Preferred catalysts are those sold under the designation MK-101 by Haldor Topsøe A/S, Denmark and under the designation 51/3 by ICI Katalco.

For ammonia synthesis preferred catalysts include Fe impregnated with non-reducible oxides of K, Ca, Al, Be, Ce, Si or mixtures thereof.

For methanol synthesis, the reaction vessel is preferably maintained at a pressure of between about 30 bar and about 100 bar, even more preferably about 50 bar to about 80 bar. The reaction temperature is normally between about 200° C. and about 300° C., for example between about 250° C. and about 280° C.

For ammonia synthesis, the reaction vessel is typically maintained at a pressure of up to about 600 bar. Pressures of between about 70 bar and about 150 bar are preferred and a typical pressure is about 140 bar. In ammonia synthesis temperatures of between about 400° C. and about 550° C. are typically used.

It is desirable that the arrangement of diaphragm, trough members and apertures between adjacent catalyst beds shall not give rise to an undesirable pressure drop as the reaction mixture passes from the vapour collection chamber to the vapour redistribution chamber. Hence the cross-section of the tortuous pathway should be of a size sufficient not to cause an excessive throttling of the flow of the reaction mixture through the reactor. In particular the respective numbers and sizes of the respective first, second and third apertures should be selected so as not to give rise to an unacceptable pressure drop across the diaphragm. It is within the competence of the person skilled in the art to calculate the pressure drops caused by particular geometric arrangements of quench gas conduits for any given set of number, size and arrangement of first, second or third apertures and to select an appropriate number and size of apertures in accordance with such calculations.

In one preferred embodiment of the invention, the reactor further comprises baffle means adjacent the diaphragm extending across the interior of the pressure vessel and having at least one breach through which the vaporous reaction mixture is constrained to pass. The baffle means may be located upstream or downstream of the diaphragm. More than one baffle means may, if desired, be provided between any given pair of catalyst beds. In this case, baffle means may be provided both upstream and downstream of the diaphragm. It is preferred that baffle means be provided upstream of the diaphragm.

The purpose of the baffle means is to cause transverse mixing of the vaporous reaction mixture so that any temperature inhomogeneity in the mixture entering a vapour collection chamber, if the baffle means is provided upstream of the diaphragm, or a vapour redistribution chamber, if the baffle means is provided downstream of the diaphragm, is eliminated or reduced.

Thus, this arrangement has the additional advantage that if the reaction mixture passing into the vapour collection chamber or the vapour redistribution chamber between any given pair of catalyst beds has a non-homogenous temperature profile, its passage through the baffle means causes some homogenisation of this profile due to self-mixing of the reaction mixture as it passes through the at least one breach in the baffle means.

The baffle means conveniently comprises a number of baffle plates which are bolted or welded together to provide a substantially closed surface to the vaporous reaction mixture, negotiable only through the at least one breach.

The at least one breach may comprise one or more grills forming part of the baffle means, each grill comprising a series of slots or apertures in the baffle means. In this arrangement, it is important that the baffle means in the region of the slots or apertures be of a thickness sufficient to create a tunnelling effect as a vaporous reaction mixture passes therethrough causing a degree of homogenisation of the reaction mixture to occur as it passes through the slots or apertures.

If the baffle means is of circular cross section, a single grill traversing the baffle means diametrically may be provided. Alternatively a plurality of symmetrically arranged grills may be provided. These may, for example when the reactor is of circular transverse cross section, lie along chords of the baffle means. Alternatively, grills may be arranged at various points of the baffle means. It will be understood by those skilled in the art that the purpose of these grills is at least partially to homogenise the vaporous reaction mixture as it passes through the baffle means. Accordingly, there is a multitude of possible arrangements of a grill or grills which would achieve this aim. The examples given above are not intended to be exhaustive and it is not necessary to describe in detail every one of these arrangements since the skilled person will understand the likely efficacy of any particular arrangement.

As the intercepted vaporous reaction mixture meets the closed surface provided by the baffle means, it is deflected and flows over the closed surface of the baffle means until it encounters the breach. The impact of the vaporous mixture upon the surface causes turbulent mixing of the mixture. This homogenises the mixture to some extent and helps prevent the formation or persistence of localised pockets of hot or cold gas in the reaction mixture. It is desirable to avoid the formation of hot pockets of gas because of the deleterious effect such pockets may have on the performance and life of the heterogeneous catalyst in the next successive catalyst beds. Cold pockets are also undesirable because they may snuff the reaction.

The reaction mixture can negotiate the baffle means only by flowing through the breach towards the inlet end of the next successive catalyst bed. This promotes transverse mixing of the vaporous reaction mixture flowing towards and through the breach from different directions.

In another preferred embodiment of the invention, there is provided a barrier means in association with the at least one breach of the baffle means. The efficacy of the process in which the reaction mixture is homogenised to some extent on passing through the breach is improved by the provision of such barrier means associated with the or each breach. The barrier means may be provided above or below the baffle means, or both above and below the baffle means. The barrier means has the important and advantageous effect of promoting turbulent mixing of the vaporous reaction mixture as it negotiates the baffle means. Vaporous reaction mixture flowing transversely across the baffle means and through the breach encounters the barrier means and is prevented thereby from flowing through the breach without substantially altering its transverse direction of flow.

The barrier means preferably comprises a deflection surface standing out from the plane of the baffle means, providing a barrier to transverse flow of the vaporous reaction mixture.

There are many arrangements of barrier means which may be envisaged by the skilled person to promote turbulent mixing of the vaporous reaction mixture. The following embodiments are not therefore intended to be exhaustive. One embodiment of barrier means comprises a walled member having an opening at one end thereof to allow ingress of a vaporous reaction mixture. The walled member may comprise three planar wall surfaces joined at right angles to each other to form three sides of a rectangular pen. This type of barrier means is arranged so that it straddles the at least one breach. The breach may comprise an open gap in the baffle means. Alternatively, it may comprises a grill as described above. A vaporous reaction mixture entering the pen at its open end is subjected to turbulent mixing around the walls thereof. This mixing occurs before or after passing through the breach, depending on whether the pen is situated above or below the breach. Both arrangements are possible.

The pen may, if desired, be provided with a cover so that vapour can only enter or escape the pen via its open end or via the diaphragm breach.

Accordingly one preferred embodiment of the invention utilises a baffle means formed from a baffle plate, or a number of baffle plates, in which a grill forms the at least one breach and the barrier means comprises an open-ended three-walled pen arranged over or under the grill and secured to the baffle plate or plates, for example by means of bolts, rivets or a weld.

In one preferred embodiment of the invention, a plurality of open-ended, three-walled pens are arranged along the length of the breach, each pen having its open end oriented at 180° to its neighbour or neighbours. In this way, a vaporous reaction mixture flowing across the closed surface of the baffle means encounters a turbulent mixing zone within a pen, regardless of its original direction of flow.

If a series of barrier means is provided, it may be preferred to seal any gaps between neighbouring barrier means to prevent the vaporous reaction mixture from flowing therethrough.

In another embodiment of the invention, the barrier means is formed as a raised wall running along and adjacent the length of the breach, the wall having a series of slots or apertures along its length to allow passage of a vaporous reaction mixture therethrough. Preferably, two parallel walls, one on either side of the breach, are provided. In this arrangement, the slots or apertures in each wall may be linearly offset with respect to each other. Thus, a vaporous reaction mixture flowing across the closed surface of the baffle means and through an aperture in one wall of a pair towards the other wall of the pair encounters a closed surface on the other wall. Impact of the vapour upon this closed surface facilitates turbulent mixing of the vaporous reaction mixture flowing between the walls.

The wall or walls may be provided either above or below the baffle means, or both above and below the baffle means.

In another embodiment of the invention, the barrier means is provided in the following manner. The baffle means is originally formed without a breach. A slot with a linear axis and castellated plan is cut in the baffle means to provide a series of interleaving fingers. These fingers may then be bent upwardly, or downwardly, out of the plane of the baffle means to provide a series of raised, or lowered, interleaving fingers. In this case, the breach is provided by the slot cut in the baffle means and the barrier means is provided by the fingers outstanding from the plane of the baffle means. It is also possible to provide mating castellated edges on a pair of baffle plates which can then be joined in the plane of each baffle plate to obtain this type of baffle means.

The invention further provides a continuous process for conducting an exothermic vapour phase reaction, which process comprises:

a) supplying to a pressure vessel via inlet means therefor a gaseous reactant or reactants;

b) maintaining in the pressure vessel temperature and pressure conditions effective for production of a desired product by means of the exothermic vapour phase reaction;

c) allowing the gaseous reactant or reactants to flow in turn through a plurality of beds of a heterogeneous catalyst effective for catalysis of the exothermic vapour phase reaction, each bed being supported within the pressure vessel by a respective support means;

d) collecting vaporous reaction mixture exiting a first bed of each successive pair of beds in a vapour collection chamber which is separated from a corresponding downstream vapour redistribution chamber for redistributing vapour over the inlet end of the other bed of the respective pair by a diaphragm extending across the interior of the pressure vessel and separating the vapour collection chamber from the vapour redistribution chamber;

e) allowing vaporous reaction mixture to pass from the vapour collection chamber to the vapour redistribution chamber by means of a tortuous passageway formed by at least one pair of nested trough members comprising an inner trough member and an outer trough member associated with and extending at least partially across the diaphragm, the inner trough member opening to the vapour collection chamber and having one or more first apertures along the length of the inner trough member and the outer trough member communicating laterally on each side with the vapour redistribution chamber by means of one or more second apertures opening laterally of the outer trough member along a respective side thereof, the space between the inner trough member and the outer trough member providing said tortuous passageway for vapour from the vapour collection chamber to the vapour redistribution chamber through the at least one first aperture, through the space between the inner trough member and the outer trough member, and then through the at least one second aperture to discharge laterally into the vapour redistribution chamber;

f) supplying quench gas to the vaporous reaction mixture passing through the diaphragm by means of a quench gas conduit associated with each pair of trough members, the quench gas conduit being provided with one or more third apertures along its length arranged to discharge quench gas into the vapour flowing along the tortuous pathway; and g) recovering from the pressure vessel via outlet means provided downstream from the final catalyst bed a vaporous product stream containing said product.

In a preferred process according to the invention there is further included the step of providing, adjacent the diaphragm, baffle means extending across the interior of the pressure vessel and having at least one breach therethrough, and constraining the vaporous reaction mixture to pass through the baffle means.

In order that the invention may be clearly understood and fully carried into effect, a number of embodiments thereof will now be more particularly described with reference to the accompanying drawings, in which:

FIGS. 13, 13a, 13b, 14, 15, 16 and 16a are partial and schematic cross sections on line I—I of modified forms of the reactor shown in FIG. 6;

FIG. 17 is a partial and schematic perspective of the barrier means and breach of the baffle means of FIGS. 16 and 16a.

For the avoidance of doubt, FIGS. 1 to 18 are intended only as an aid to understanding the invention and are not to be construed as limiting the scope of the invention with regard to the precise number of catalyst beds or positioning thereof, the shape of the reactor vessel or any of its ancillary features, the precise shape or positioning of the quench gas conduits, trough members, apertures and diaphragms, other than those aspects of shape and position which are described more particularly below, or any other feature of the reactor which is not expressly claimed below.

Figure 1:
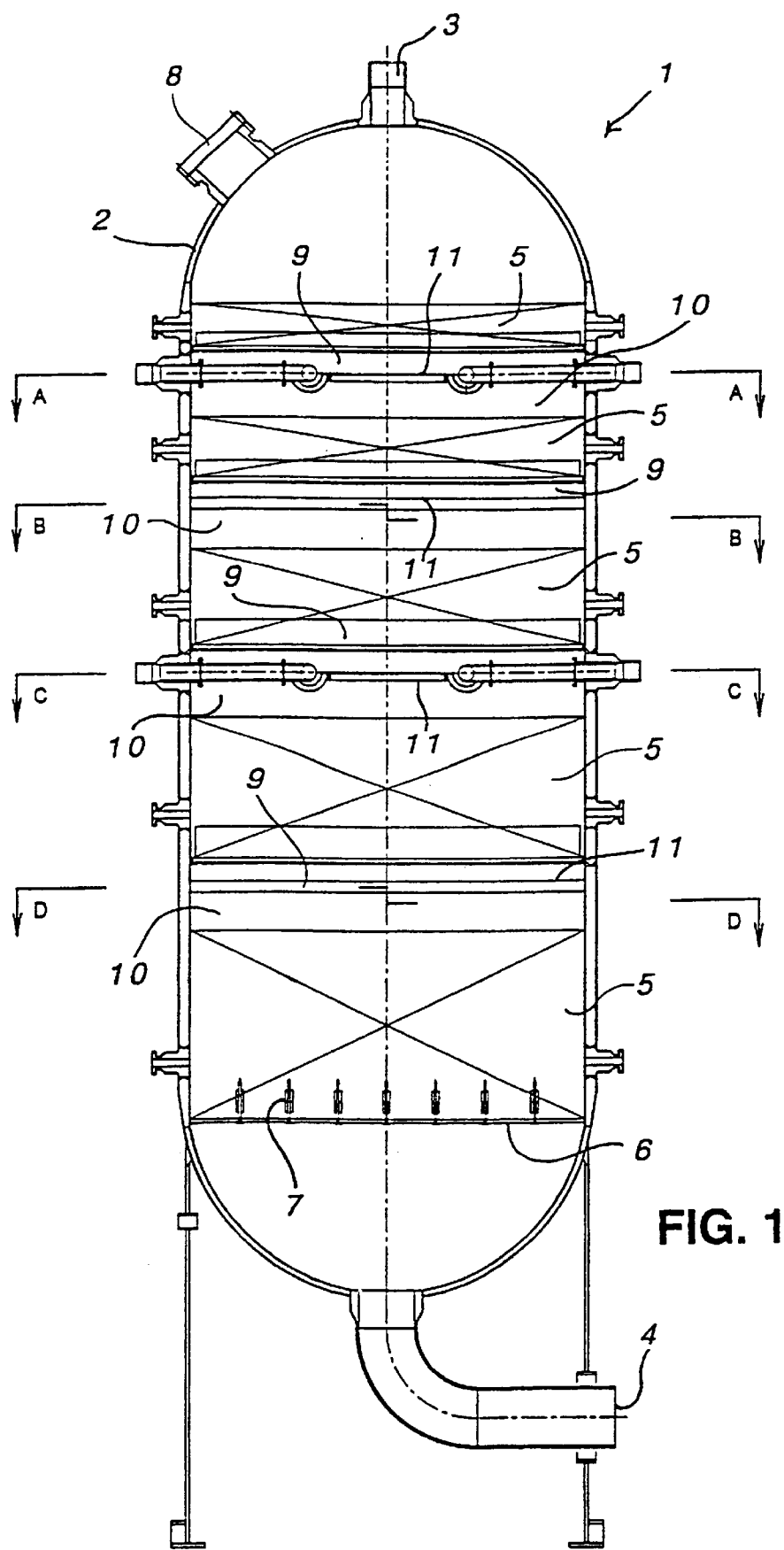
FIG. 1 is a simplified vertical cross-sectional diagram of a reactor designed in accordance with the present invention.

Referring to FIG. 1, reactor 1 comprises an outer pressure shell 2 provided with a top inlet 3 for incoming synthesis gas or vapour and a bottom outlet 4 for a vaporous product stream. Reactor 1 is provided with five beds 5 of a heterogeneous methanol synthesis catalyst, each bed being supported by a respective catalyst support grating 6.

A number of parallel catalyst support beams 7 project upwardly into each bed 5 to provide lateral support for the catalyst grating 6 and for the catalyst of bed 5. For clarity, support beams 7 are shown only on bottommost grating 6 in FIG. 1. Reference numeral 8 indicates a manhole through which catalyst may be loaded into and unloaded from reactor 1. Below each catalyst bed 5 other than the bottommost one is a vapour collection chamber 9, whilst above each catalyst bed 5 other than the topmost one is a vapour redistribution chamber 10. Each vapour collection chamber 9 is divided from its adjoining vapour redistribution chamber 10 by a diaphragm 11.

Figure 2:
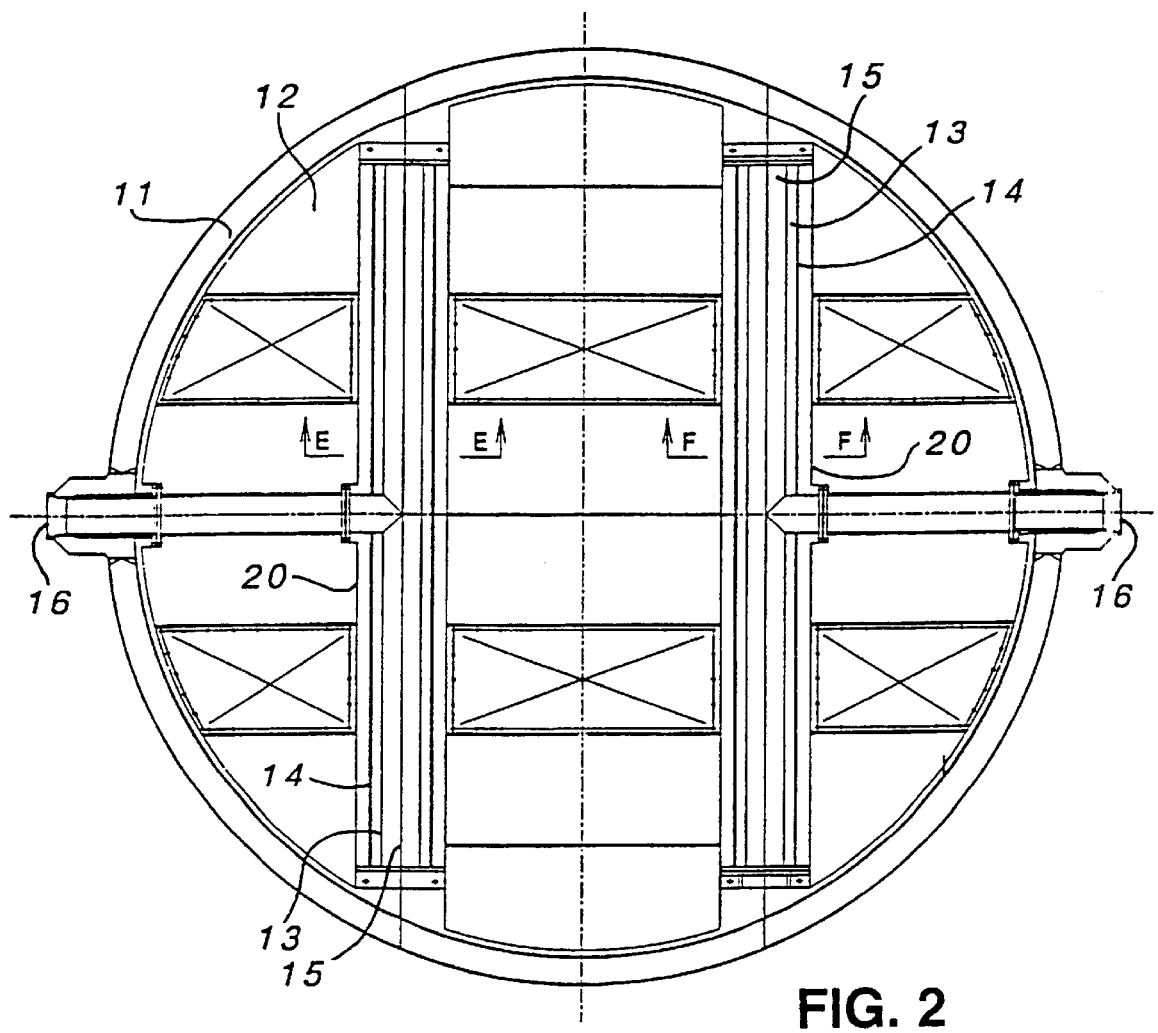
FIG. 2 is a horizontal cross-section on line A—A or C—C of FIG. 1.

Referring to FIG. 2, it can be seen that diaphragm 11 comprises a number of baffle plates 12 which prevent the passage of gas from vapour collection chamber 9 to vapour redistribution chamber 10 (FIG. 1) except through open channels 13 defined by troughs 14 and conduits 15. Conduits 15 extend along chords of diaphragm 11 so as to divide it into segments and carry quench gas from inlet pipes 16. As can be seen from FIG. 2 each inlet pipe 16 and its conduit 15 form a T-shape. Conduits 15 are symmetrically arranged with respect to a central axial plane of reactor 1. Any number of conduits 15 can be employed in the reactor of the invention but, if an odd number is to be used, then one of the conduits 15 should preferably occupy a line bisecting diaphragm 11.

The quench gas supplied via conduit 15 may be an inert gas but is more usually fresh or recycled synthesis gas or a mixture thereof. It is at a lower temperature than the gas exiting catalyst bed 5 above the respective diaphragm 11. Typically it is at least about 100° C., up to about 200° C. or more, cooler than that exist gas temperature. (If a reactor of similar design is used in the synthesis of ammonia, the quench gas temperature is desirably about 200° C. to about 400° C. lower than the temperature of the reaction mixture collected in the vapour collection zone.) The purpose of introducing such quench gas is to provide a temperature quench thereby lowering the average temperature of the vapour recovered from an upstream catalyst bed 5 (FIG. 1), the temperature of the vapour having been raised in passage through bed 5 by the exothermic reaction of synthesis gas. The temperature quench thus achieved between successive catalyst beds 5 serves to adjust the inlet temperature conditions to the next bed 5 away from the equilibrium temperature. This allows the product forming reactions to predominate as the reaction mixture passes on into the next bed. The quench gas must accordingly be supplied in conduits 15 at a lower temperature than that of the vapour entering troughs 14 from respective vapour collection chamber 9 (FIG. 1).

Conduits 15 have a series of axial slots or holes 17 (FIG. 3) on their lowermost surfaces, which slots or holes permit egress of quench gas into troughs 14. Troughs 14 are provided with a series of axial slots or holes 18 (FIG. 3) which are substantially co-radial with slots or holes 17 to allow direct passage of quench gas from conduits 15 into mixing zones 19 (FIG. 3) situated in the respective radial spaces defined between troughs 14 and lower co-axial troughs 20.

Hot vapour recovered from catalyst bed 5 (FIG. 1) flows into the respective vapour collection chamber 9 (FIG. 1) and into respective open channels 13 between troughs 14 and conduits 15. The hot vapour in channels 13 becomes entrained in the flow of quench gas from slots or holes 17 and passes through slots or holes 18 (FIG. 3) into mixing zones 19. Troughs 20 are provided with a series of axial slots or holes 21 (FIG. 3) to allow egress of a temperature-quenched gas stream into the vapour redistribution chamber 10 (FIG. 1). However, slots or holes 21 are not radially aligned with slots or holes 17 and 18 but are radially offset with respect thereto so that the quench gas and entrained hot vapour stream entering mixing zones 19 are directed at respective closed surfaces on troughs 20, on which the gas stream impacts, causing turbulent mixing of the quench gas with the vapour within mixing zones 19. The mixed gas stream exits laterally into vapour redistribution chamber 10 (FIG. 1) via slots or holes 21 which are symmetrically disposed with respect to the axis of each trough 20. Moreover the gas stream is constrained to follow a tortuous pathway from entering into channels 13, through holes or slots 18, then through mixing zones 19 and out through holes or slots 21. The symmetrical disposition of slots or holes 21 is important because it ensures that the mixed gas stream is evenly distributed into vapour redistribution chamber 10 (FIG. 1). Uneven distribution of the vapour may lead to uneven reaction through the next catalyst bed 5, giving rise to inefficient utilisation of the catalyst and to premature catalyst deterioration due to hot-spot formation or to snuffing of the reaction through cold spot formation.

Quenched methanol-containing vapour stream passes into vapour redistribution chamber 10 and into a further catalyst bed 5. Upon recovery from this further catalyst bed 5, the hot methanol-containing vapour stream is once again quenched in passage from a further vapour collection chamber 9 to a further vapour redistribution chamber 10 through a quenching system similar to that described above.

The quench gas conduits 15 of axially successive diaphragms 11 are preferably radially offset with respect to each other about the vertical axis of reactor 1. Thus, the topmost and third from top diaphragms 11 and associated quench gas conduits 15 in FIG. 1 are orientated identically to each other but quench gas conduits 15 of the second and fourth diaphragms 11 (from the top of reactor 1) are radially offset by 90° about the vertical axis of reactor 1 with respect to quench gas conduits 15 of the topmost and third from top diaphragms 11.

Figure 4:
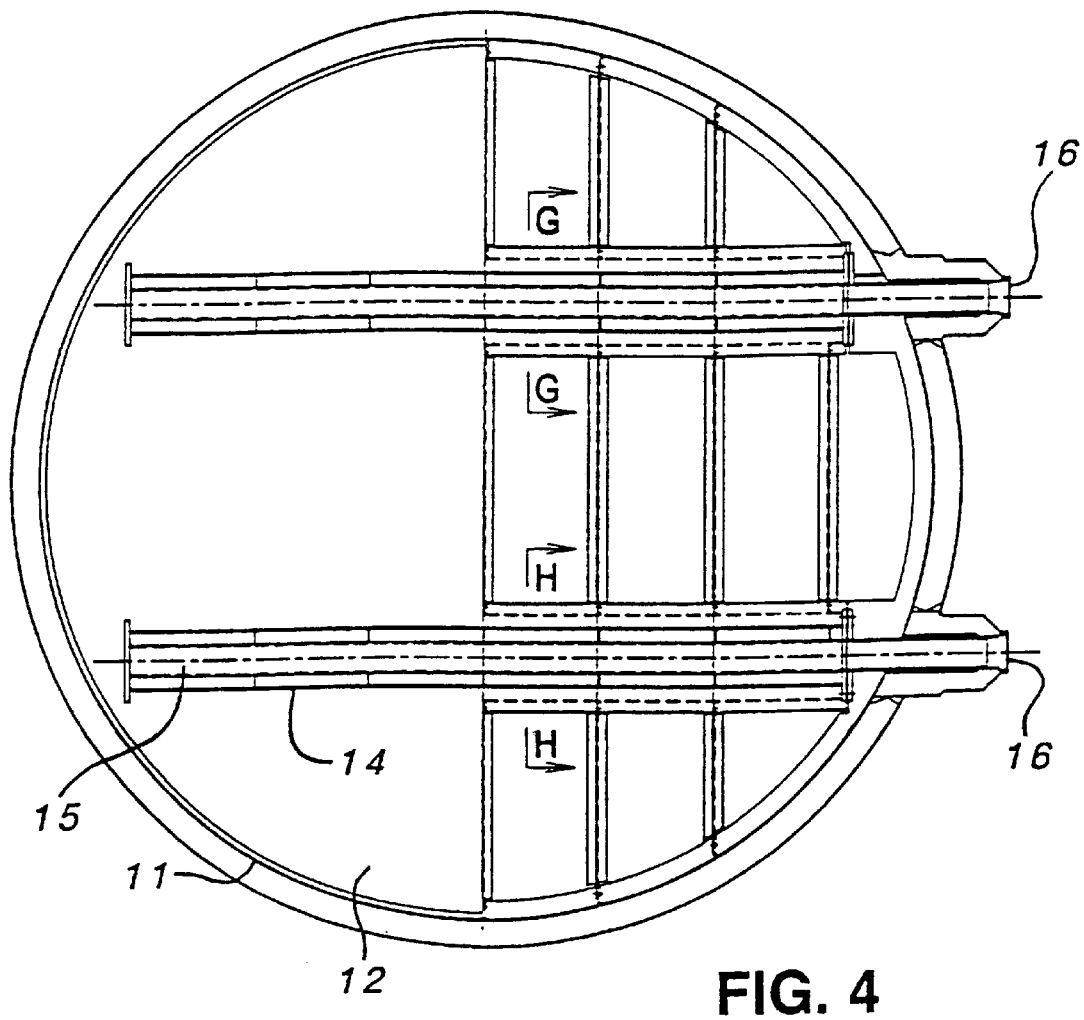
FIG. 4 is a horizontal cross-section through a second form of reactor, corresponding to a cross-section on line B—B or D—D of FIG. 1.

FIG. 4 is a horizontal cross section through a modified form of reactor on a line corresponding to line B—B or D—D of FIG. 1, The reactor of FIG. 4 differs from that of FIG. 2 in that, instead of quench gas inlet pipes 16 being joined to conduits 15 at a T-joint, they are in line with conduits 15.

Baffle plates 12 are shown in FIG. 4 forming diaphragm 11 which divides vapour collection chamber 9 from vapour redistribution chamber 10 (FIG. 1). Hot vapour from vapour collection chamber 9 enters troughs 14 and becomes entrained in the downward flow of quench gas emerging from conduits 15. Quench gas is supplied via inlet pipes 16. The quench gas sparging and mixing in the reactor of FIG. 4 occurs in a substantially identical manner to that occurring in the reactor of FIG. 2.

The radial offsetting of successive quench gas conduits 15 relative to each other about the vertical axis of reactor 1 has the additional advantage that any temperature inhomogeneity in the quenched gas stream recovered from a catalyst bed 5 is not perpetuated by subsequent mixing through the subsequent catalyst bed 5. This feature therefore substantially eliminates the persistent development of hot or cold spots in a downstream bed 5 as a result of local hot or cold spot formation in an upstream bed 5.

Figure 3:
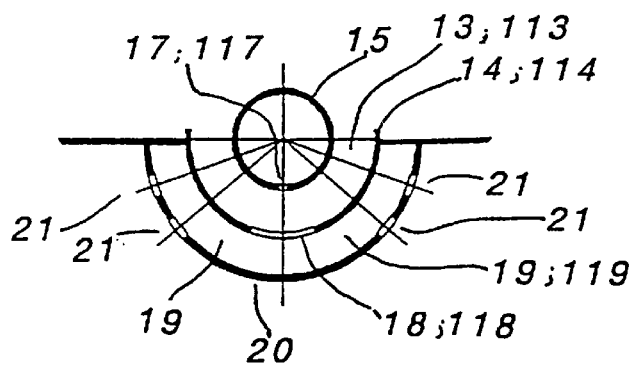
FIG. 3 is a cross section on lines E—E or F—F of FIG. 2 or on line G—G or H—H of FIG. 4.
Figure 5:
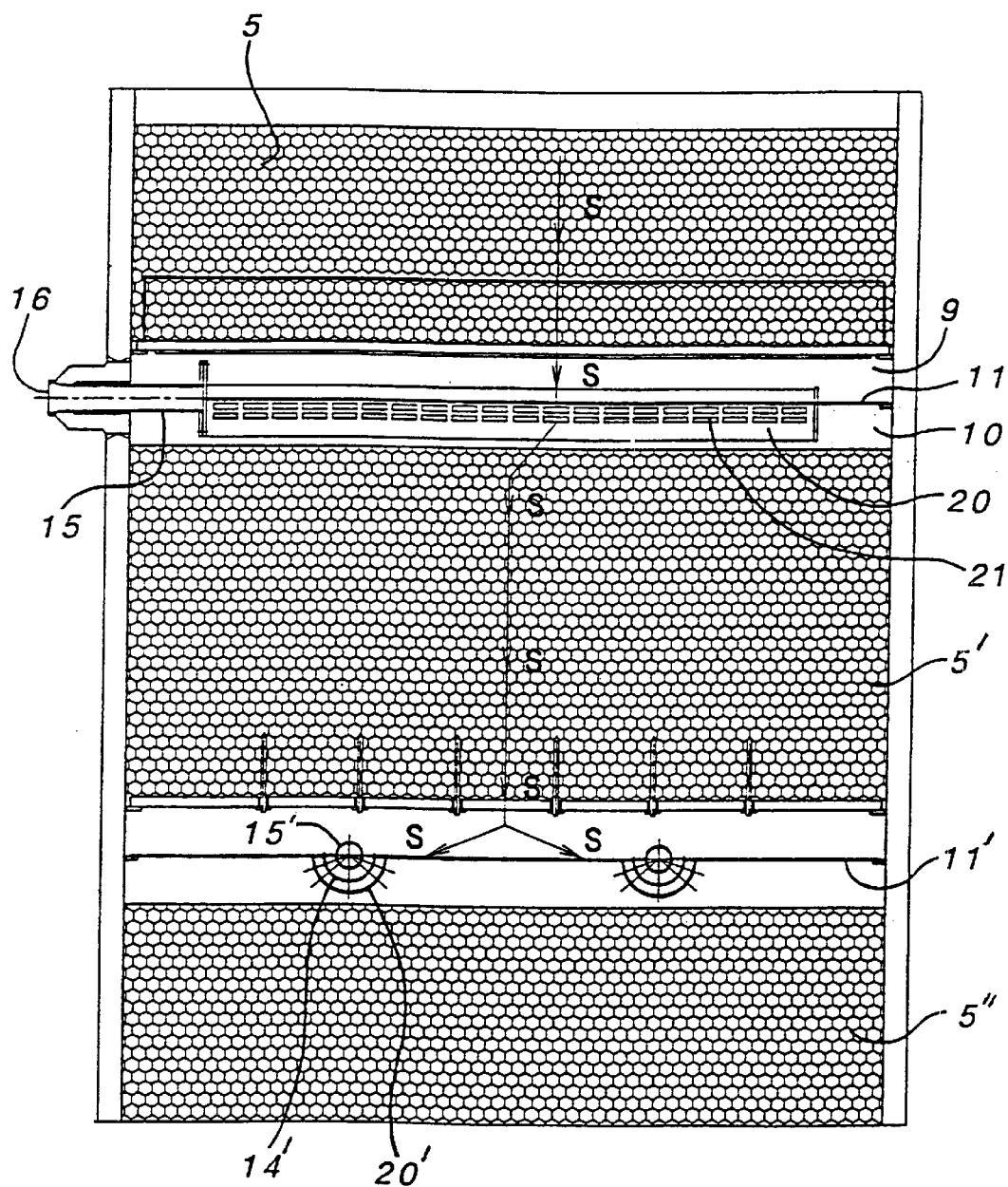
FIG. 5 is an expanded vertical cross-section view of part of the reactor shown in FIG. 1.

The radial offsetting of successive quench gas conduits 15 is perhaps best illustrated in FIG. 5 which shows a cross-sectional view of part of the reactor of FIG. 4 (that is the reactor of FIG. 1 with colinear quench gas conduits 15 and inlet pipes 16). Hot vapor is recovered from catalyst bed 5 in vapour collection chamber 9 and flows into open channels 13 (FIG. 3) bounded by conduits 15 and troughs 14 (FIG. 3). Quench gas is supplied in conduits 15 via inlet pipes 16. The hot vapour from the vapour collection chamber 9 flows via channels 13 into troughs 14 and becomes entrained in the stream of quench gas flowing from conduits 15 through slots 17 and 18 (FIG. 3). The hot vapour is therefore carried into mixing zones 19 by an eductive effect. The quenched gas stream exits from troughs 20, after turbulent mixing, laterally through slots 21 which are arranged in two rows on each side of troughs 20. The two rows of slots 21 are symmetrically arranged in each trough 20 with respect to the vertical plane of symmetry through slots 17 and 18. The symmetrical arrangement of slots 21 ensures homogeneous distribution of the quenched gas stream into the vapour distribution chamber 10. It also ensures that the entrained gas streams entering trough 20 via slots 18 are mixed equally irrespective of the direction in which they impact upon the closed wall of trough 20. The quenched gas passes on through bed 5' and the resulting reaction mixture is then similarly mixed with quench gas in passage through diaphragm 11'. Conduits 15' and troughs 14' and 20' are radially offset by an angle of 90° about the vertical axis of the reactor with respect to conduits 15 and troughs 14 and 20 respectively. Mixing takes place in the same way as described above. However, due to the redistribution of gas that occurs in passage from vapour collection chamber 9 along the tortuous pathway to holes or slots 21, a local pocket of hot or cold gas following the route indicated by line S on FIG. 5 would not persist in catalyst bed 5'', as might be the case if the conduits 15' and troughs 14' and 20' were respectively aligned in a vertical plane with conduits 15 and troughs 14 and 20.

In FIG. 5 the angle of radial offset between conduits 15 and 15' about the vertical axis of the reactor is 90°. It is alternatively possible to utilise a smaller angle of offset, e.g. 45° or 60°, between conduits 15 and 15'.

One advantage of the invention is that any pressure drop occurring on passage of the synthesis gas mixture through diaphragm 11 can be at least partially restored by supplying quench gas in conduit 15 in a manner and at a pressure sufficient to increase the momentum of the gas mixture flowing along the tortuous passageway.

Figure 6:
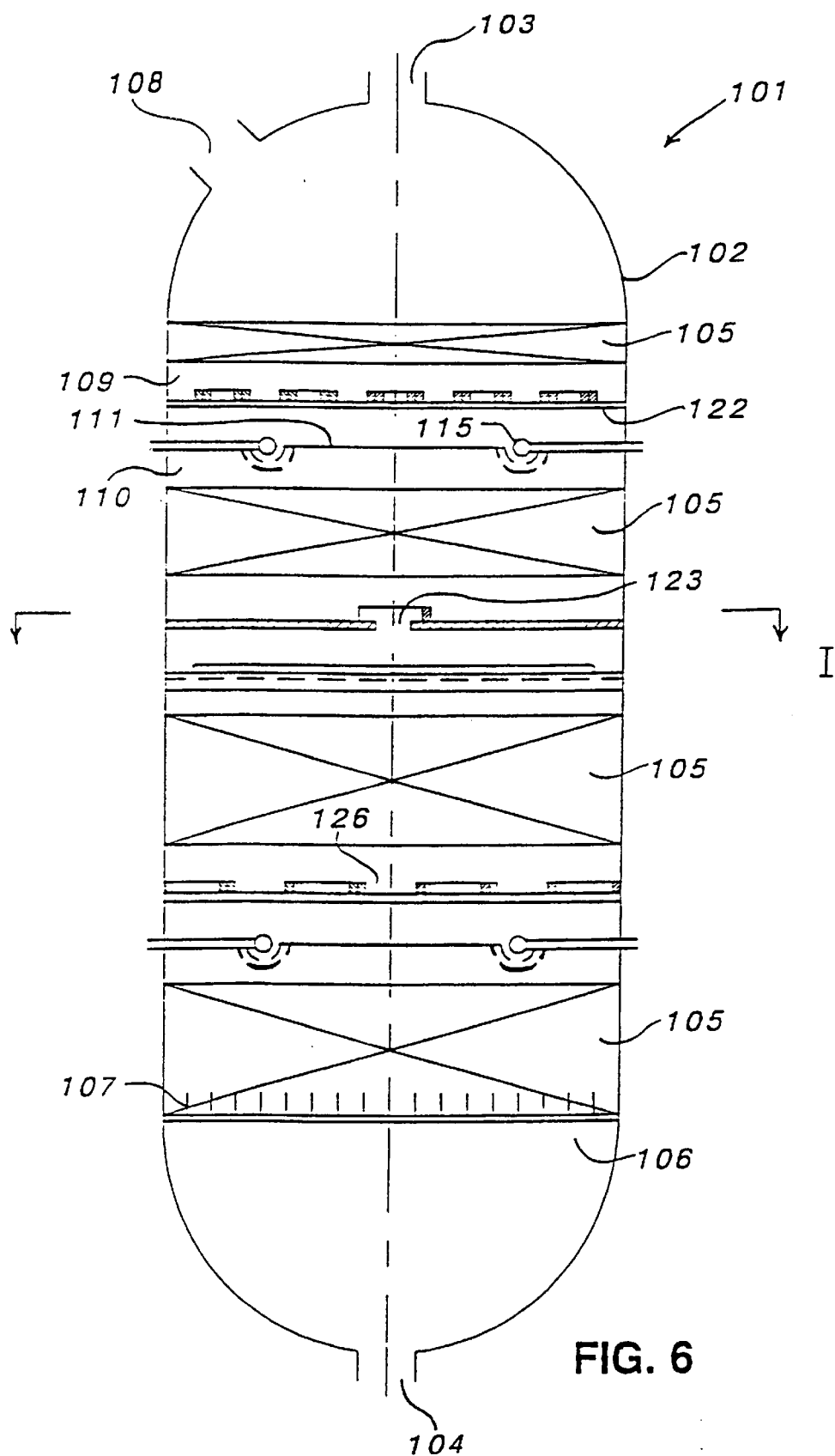
FIG. 6 is a simplified vertical cross-sectional diagram of a third form of reactor designed in accordance with the present invention.

Referring now to FIG. 6, there is shown a second embodiment of the invention, in which reactor 101, pressure shell 102, top inlet 103, bottom outlet 104, catalyst beds 105, support gratings 106, support beams 107 and manhole 108 are arranged substantially identically to items 1 to 8 of the reaction 1 shown in FIG. 1.

Between successive catalyst beds 105, of which there are four in reactor 101, is a vapour collection chamber 109 and a vapour redistribution chamber 110. Vapour collection chamber 109 is separated from vapour redistribution chamber 110 by diaphragm 111. Baffle means 122 is shown mounted within vapour collection chamber 109. However, it is also possible to mount baffle means 122 within vapour redistribution chamber 110. Pressure vessel 102 is substantially circular in cross section and two quench gas conduits 115 lie along parallel chords of diaphragm 111.

Figure 7:
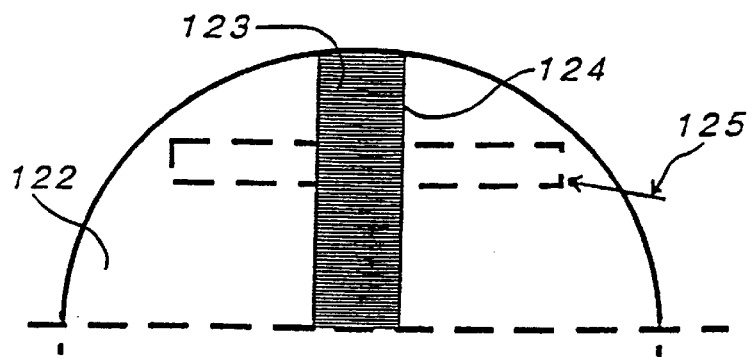
FIGS. 7, 7a, 8, 8a, 9, 10, 10a and 11 are partial and schematic cross sections on line I—I of FIG. 6, or of modified forms of the reactor shown in FIG. 6.
Figure 7A:
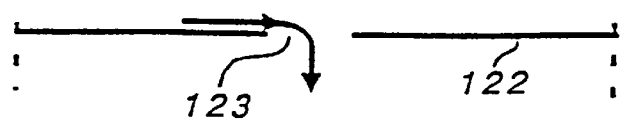

FIG. 7 shows half of a cross section on line I—I of FIG. 6. Baffle means 122 is of circular cross section and is provided along its diameter with a breach 123 comprising a grill 124. Reference numeral 125 in FIG. 7 represents in outline the presence of a quench gas conduit 115 and associated nested trough members beneath baffle means 122. Quench gas conduit 115 is one of a pair of such conduits, the other conduit of the pair lying along a chord of diaphragm 111 parallel and symmetrically arranged with respect to the conduit shown as reference numeral 125. FIG. 7a shows another cross section on the whole of baffle means 122 and breach 123.

Referring to FIG. 7, breach 123 comprises a series of parallel longitudinal slotted apertures forming a grill 124, in baffle means 122.

Although grill 124 shown in FIG. 7 comprises a series of parallel slots, it will be apparent to the skilled person that a number of alternative arrangements can be envisaged. For example, grill 124 may comprise a symmetric array of circular holes, or may be formed as a mesh structure, for example resembling chicken wire.

Figure 8:
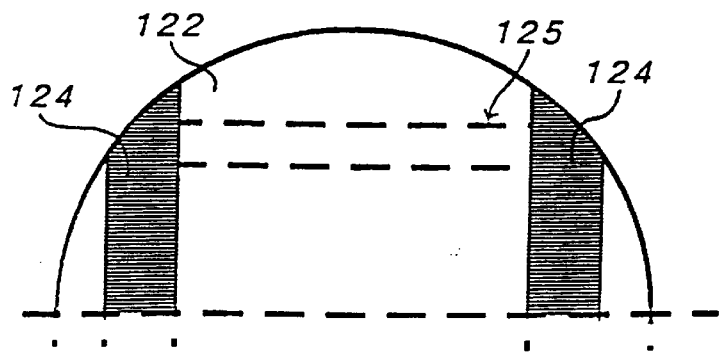
Figure 8A:
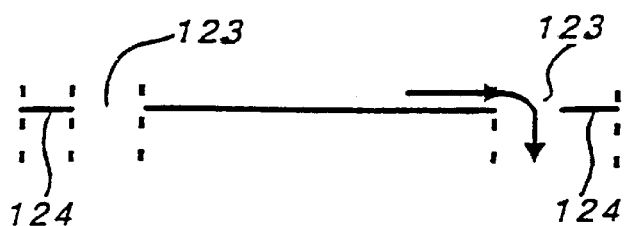

FIGS. 8 to 17 show alternative arrangements of baffle means 11. In FIG. 8 baffle means 122 has two grills 124 arranged on parallel chords of baffle means 122. FIG. 8a shows another cross section on baffle means 122.

Figure 9:
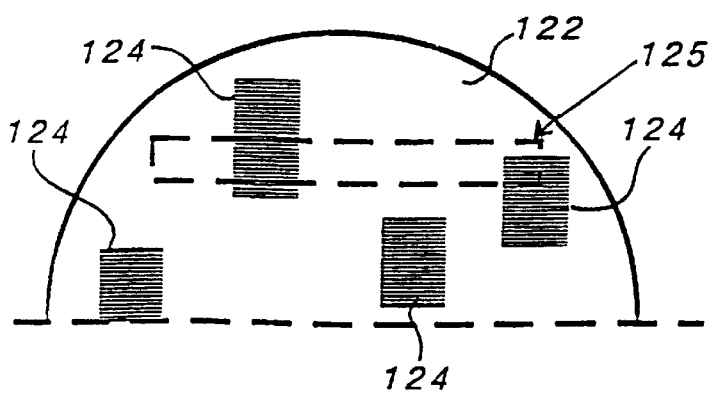

In FIG. 9, a plurality of grills 124 are shown in a spaced apart arrangement on baffle means 122. Many other such arrangements can be envisaged by those skilled in the art.

Figure 10:
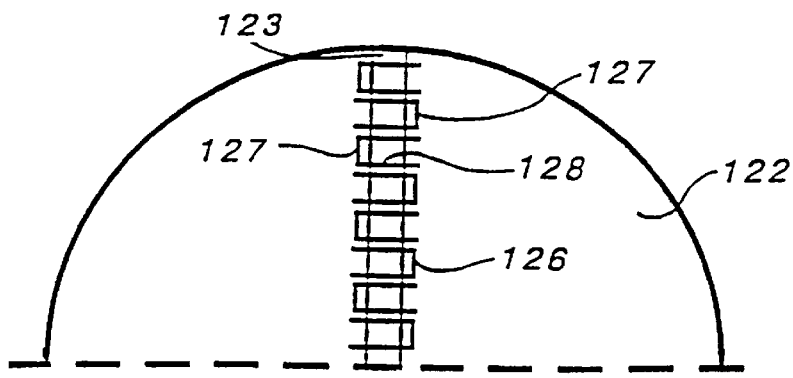
Figure 10A:
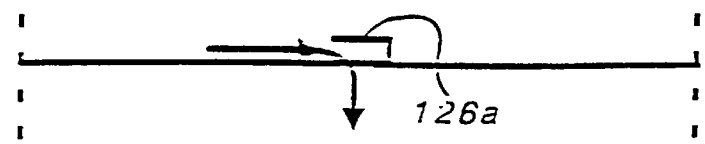

FIG. 10 shows baffle means 122 and breach 123 which is simply an open gap in baffle means 122. No grill is present. Breach 123 is overlaid with a series of barrier means 126. Barrier means 126 is a pen mounted on baffle means 122. Each pen 126 has a lid 126a, which is shown in FIG. 10a, an end wall 127 and two side walls 128.

Figure 11:
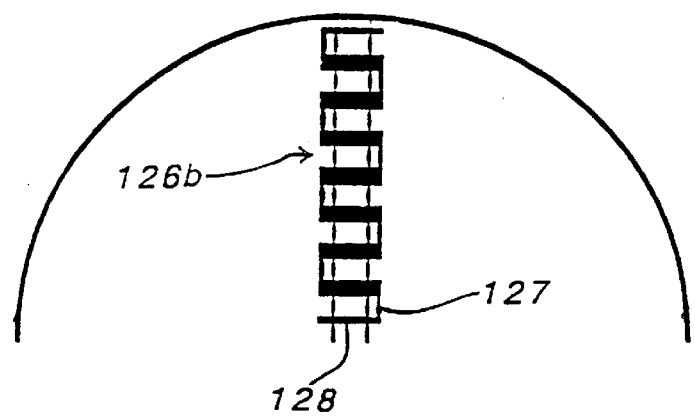

FIG. 11 shows an alternative embodiment of the pen arrangement shown in FIG. 10, in which the barrier means 126b is a pen having an end wall 127 and side walls 128. However, no lid is provided. In the embodiment of FIG. 11, the gaps between neighbouring pens 126b have been sealed to prevent the flow of vaporous reaction mixture therebetween. Vaporous reaction mixture cannot thereby flow across the closed surface of baffle means 122 without impacting upon an upstanding wall 127 or 128. An event which causes turbulent mixing of the vaporous reaction mixture stream.

Figure 12:
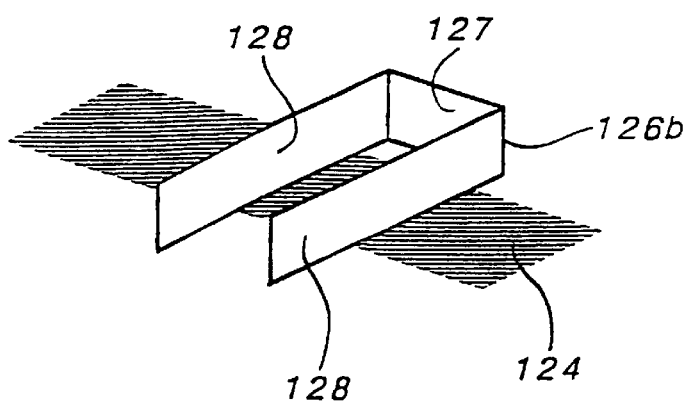
FIG. 12 is a partial and schematic perspective of a single barrier means and breach of the baffle means of FIGS. 10 and 11.

FIG. 12 shows, in perspective, a detail of a modified version of the baffle means of FIG. 11. In the embodiment of FIG. 12, the baffle means is breached by a diagonally slotted grill 124 and is overlaid by a series of barrier means 126b, only one of which is shown in FIG. 12.

In FIGS. 10, 10a, 11 and 12, pens 126 are shown as open-ended rectangular enclosures into which vaporous reaction mixture may flow and become turbulently mixed by impaction against one or more of upstanding walls 127 and 128 and, if present, lid 126a, before passing through baffle means 122 via breach 123 or 124. Many other arrangements of open-ended enclosures may be envisaged by those skilled in the art. For example, a single wall upstanding from baffle means 122 and running along the length of breach 123 may be provided, the wall being wavy in cross section along the length of the breach. Alternatively, individual open-ended enclosures 16 may be formed with arcuate, semi-circular or part-elliptical cross section. Combinations of planar and arcuate upstanding walls 127 and 128 may be envisaged. For example, open-ended enclosure 126 may comprise a planar end wall 127 and curviform side walls 128, or a curviform end wall 127 and planar side walls 128. V-plan enclosures may be used, as may open-ended pentagonal, hexagonal, heptagonal, octagonal or other plan enclosures.

FIGS. 13, 13a, 13b, 14 and 15 show alternative forms of barrier means on baffle means 122. FIGS. 13, 14 and 15 show baffle means 122 in top plan view (only half of baffle means 122 is shown). In addition, FIGS. 13a and 13b show two alternative embodiments of the invention in a side elevation (the whole of baffle means 122 being shown). Baffle means 122 is provided with a breach 123 along its diameter. Breach 123 may contain a grill or mesh structure but is simply an open gap in baffle means 122 in the embodiment shown in these Figures. On either side of breach 123, baffle means 122 is provided with a pair of parallel walls 129. In FIG. 13a the walls are upstanding from the surface of baffle means 122. In FIG. 13b the walls are protrude downwardly from the surface of baffle means 122.

Referring to FIGS. 13, 13a and 13b, each wall 129 is provided, at regularly spaced intervals along its length, with a series of apertures, or doorways, 130 which permit a vaporous reaction mixture flowing transversely across the closed surface of baffle means 122 to pass through respective wall 129 and into the space defined between walls 129 above breach 123.

In the embodiment of FIG. 13, the doorways 130 of one wall 129 of a pair of parallel walls 129 are offset linearly with respect to the corresponding doorways 130' of the other wall 129' of the pair. Thus, a vaporous reaction mixture flowing through one doorway 130 in one wall 129 of the pair impacts against the closed surface of the other wall 129' of the pair and is thus turbulently mixed before passing through breach 123. The size of individual doorways 130, 130', the spacing between doorways 130, 130' and the magnitude of linear offset between opposing sets of doorways 130, 130' may be determined by the skilled person using a scale model or computational fluid dynamics. FIGS. 13, 14 and 15 illustrate to some extent the range of possible variation. FIGS. 13 and 14 are identical, FIG. 14 indicating, by arrows a and b respectively, the width of an individual doorway 130 and the magnitude of linear offset of one particular embodiment of the invention. The width (a) of a single doorway 130 is preferably between one hundredth and one tenth of the diameter of baffle means 122. The magnitude (b) of linear offset between opposing doorways is preferably between one half of and twice width (a).

However, other embodiments of the invention may be provided in which doors 130 of opposing walls 129 are not offset with respect to each other. Such an embodiment is shown in FIG. 15.

Figure 16A:
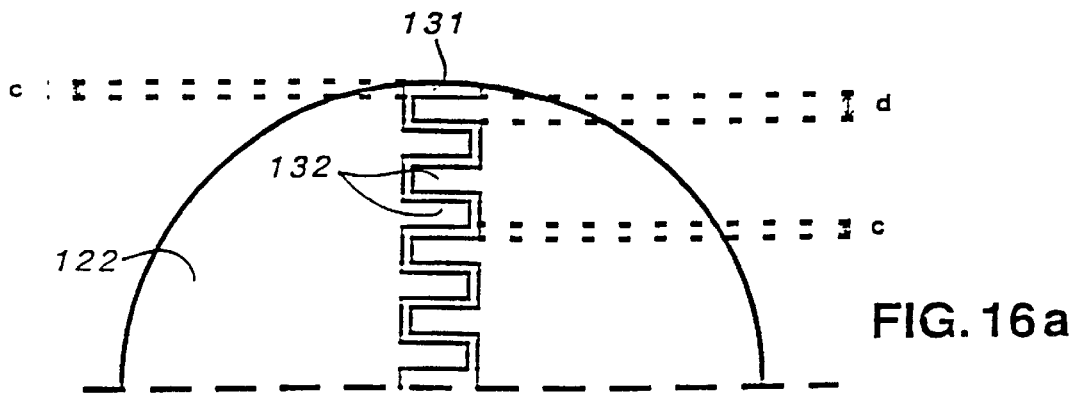
Figure 16:
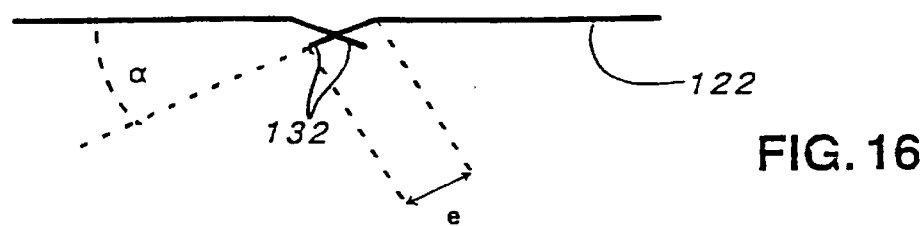
Figure 17:
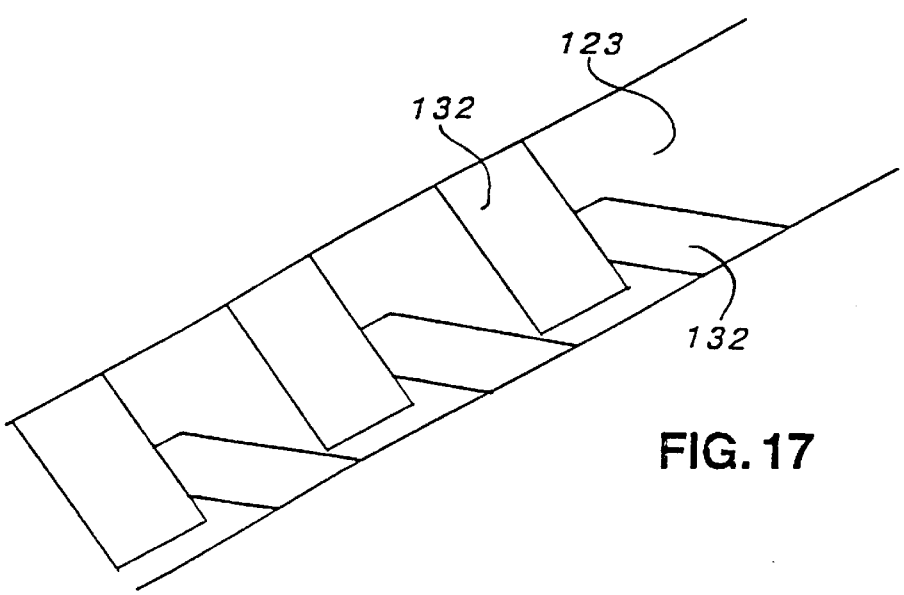

FIGS. 16, 16a and 17 show another alternative arrangement of barrier means. Baffle means 122 (only half of which is shown in the top plan view of FIG. 16) is provided with a slot 131 of castellated plan which forms the breach in baffle means 122. Castellated slot 131 corresponds to a series of interleaving fingers 132 in baffle means 122. When interleaving fingers 132 are bent out of the plane of baffle means 122, as is shown in FIGS. 16a and 17, an effective barrier means is provided. Vaporous reaction mixture flowing through slot 131 impacts upon the interleaved structure formed by fingers 132 and becomes turbulently mixed as a result. In FIG. 16 reference letters c and d indicate respectively the width of each open-ended rectangular enclosure of slot 131 and the width of each interlocking finger 132 created thereby. Preferably, width (c) is between one thousandth and one fifteenth of the diameter of baffle means 122. Preferably, the width (d) of each interlocking finger is between one hundredth and one tenth of the diameter of baffle means 122. Reference letter e indicates the length of each finger 132, which is preferably between one fiftieth and one fifth of the diameter of baffle means 122, and α indicates the preferred angle between fingers 132 and the plane of baffle means 122. Preferably, α is between 20° and 70°.

Returning to FIG. 6, hot vapour recovered from catalyst bed 105 flows into the respective vapour collection chamber 109 and, after deflection against the closed surface of baffle means 122, is channelled through breach 123. Baffle means 122 is provided on its upper surface, immediately above breach 123 with barrier means 126. Barrier means 126 is a series of open-ended rectangular walled enclosures of the type described above with reference to FIGS. 10 to 12. These help to deflect hot vapour flowing across the surface of baffle means 122 through breach 123 and also act as an impaction surface of or surfaces for turbulent mixing of the vapour. The tendency for formation of localised pockets of hot or cold vapour is thereby reduced. After passing through baffle means 122 in this way, the hot vapour stream continues on in vapour collection chamber 109 until it meets diaphragm 111.

Quenched methanol-containing vapour stream passes into vapour redistribution chamber 110 and into a further catalyst bed 105. Upon recovery from this further catalyst bed 105, the hot methanol-containing vapour stream is once again quenched in passage from a further vapour collection chamber 109 to a further vapour redistribution chamber 110 through a quenching system similar to that described above.

In the reactor of FIG. 6, diaphragm 111 and associated baffle means 122 are arranged in such a way that the longitudinal axis of breach 123 in baffle means 122 is at 90° to the longitudinal axis of each quench gas conduit 115 of diaphragm 111. This is a preferred arrangement which facilitates homogenisation of the hot vapour flowing through vapour collection chamber 109. However, it is also possible to arrange diaphragm 111 and baffle means 122 in other ways. For example, the longitudinal axis of series of breaches 123 could be arranged parallel to that of quench gas conduits 115 or could be radially offset with respect thereto by some other angle, for example 30°, 45° or 60°.

In the reactor of FIG. 6, the quench gas conduits 115 of axially successive diaphragms 111 are radially offset with respect to each other about the vertical axis of reactor 105. Thus, the topmost and lowermost diaphragms 111 and associated quench gas conduits 115 in FIG. 6 are orientated identically to each other but quench gas conduits 115 of intermediate diaphragm 111 are radially offset by 90° about the vertical axis of reactor 101 with respect to quench gas conduits 115 of the topmost and lowermost diaphragms 111. Consequently, intermediate baffle means 122 is also offset by 90° with respect to topmost and bottommost baffle means 122. However, it is also possible to arrange successive quench gas conduits 115 in parallel alignment with each other. The provision of baffle means 122 and associated breach 123 reduces the possibility that localised pockets of hot or cold gas will persist through the reactor in passage through a series of diaphragms 111 arranged with quench gas conduits 115 in parallel.

Figure 18:
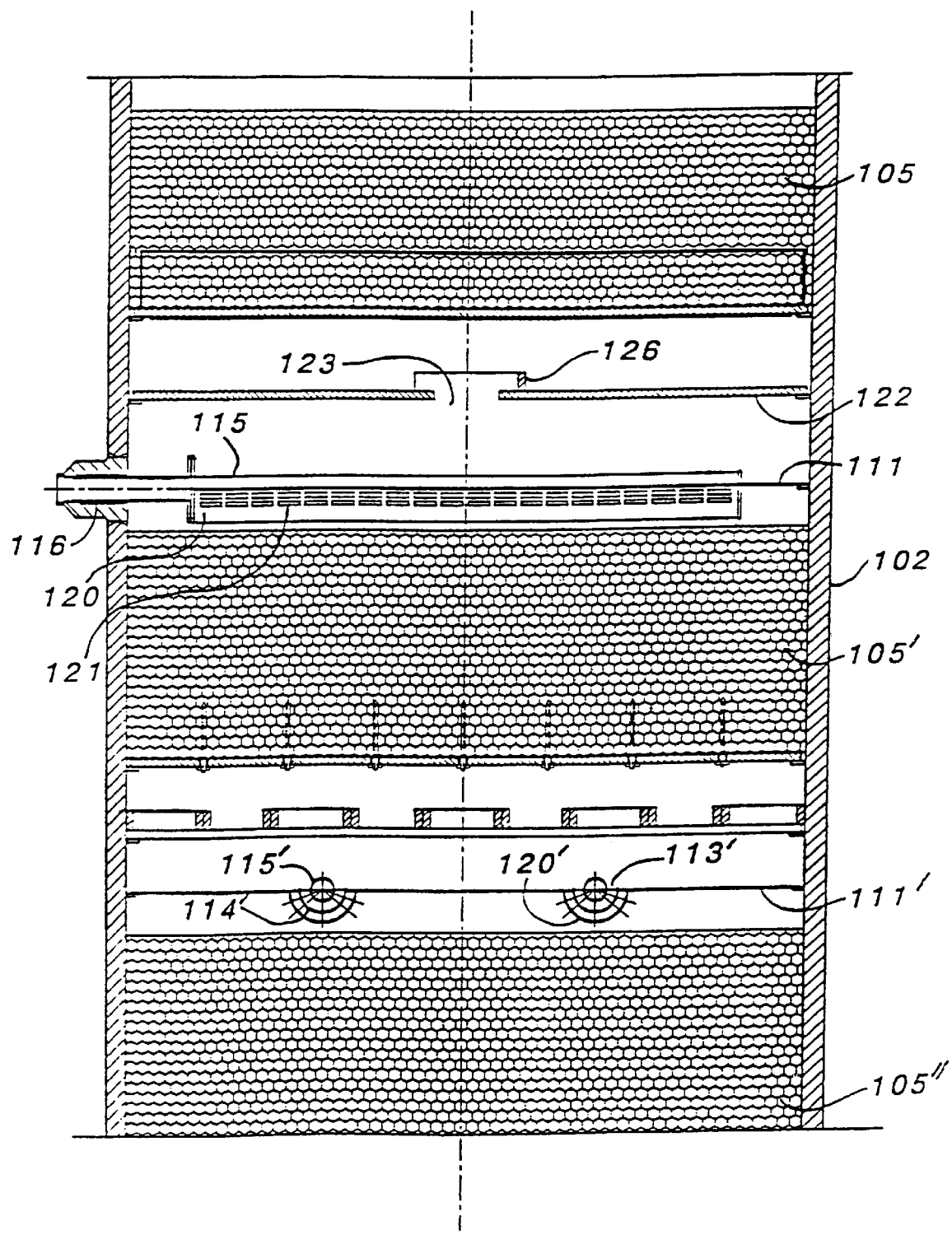
FIG. 18 is an enlarged vertical cross sectional diagram through a part of the reactor of FIG. 6.

The radial offsetting of successive quench gas conduits 115 is perhaps best illustrated in FIG. 18 which shows a vertical cross-section through part of a modified form of the reactor of FIG. 6 (in which quench gas conduits 115 and inlet pipes 126 are colinear). Hot vapour is recovered from catalyst bed 105 in vapour collection chamber 109 and flows through breach 123 in baffle means 122 after turbulent impaction against the closed surface of baffle means 122 and barrier means 126. The vapour then flows into open channels 113 (FIG. 3) bounded by conduits 115 and troughs 114 (FIG. 3). Quench gas is supplied in conduits 115 via inlet pipes 126. The hot vapour from the vapour collection chamber 110 flows via channels 113 into troughs 114 and becomes entrained in the stream of quench gas flowing from conduits 115 through slots 117 and 118 (FIG. 3). The hot vapour is therefore carried into mixing zones 119 by an eductive effect. The quenched gas stream exits from troughs 120, after turbulent mixing, laterally through slots 121 which are arranged in two rows on each side of troughs 120. The two rows of slots 121 are symmetrically arranged in each trough 120 with respect to the vertical plane of summetry through slots 117 and 118. The symmetrical arrangement of slots 121 ensures homogeneous distribution of the quenched gas stream into the vapour distribution chamber 110. It also ensures that the entrained gas streams entering trough 120 via slots 118 are mixed substantially equally irrespective of the direction in which they impact upon the closed wall of trough 120. The quenched gas passes on through bed 105' and the resulting reaction mixture is then similarly mixed with quench gas in passage through diaphragm 111'. Conduits 115' and troughs 114' and 120' are radially offset by an angle of 90° about the vertical axis of the reactor with respect to conduits 115 and troughs 114 and 120 respectively. Mixing takes place in the same way as described above.

What is claimed is:

1. A reactor for conducting an exothermic vapour phase reaction comprising:
   a) a pressure vessel having inlet means for supply of a gaseous reactant or reactants and outlet means for recovery of a product-containing stream therefore;
   b) a plurality of beds of a heterogeneous catalyst effective for catalysis of the exothermic vapour phase reaction in the path of a material passing from the inlet means to the outlet means, each bed being supported within the pressure vessel by a respective support means;
   c) a vapour collection chamber and a vapour redistribution chamber between the or each successive pair of beds, the vapour collection chamber being disposed adjacent an exit end of one bed of the pair and arranged to collect a vaporous reaction mixture from the exit end of said one bed of the pair and the vapour redistribution chamber being disposed adjacent an inlet end of the other bed of the pair and arranged to redistribute vapour over the inlet end of said other bed of the pair;
   d) a diaphragm extending across the interior of the pressure vessel and separating the vapour collection chamber from the vapour redistribution chamber for preventing flow of vapour from the vapour collection chamber to the vapour redistribution chamber;
   e) at least one pair of nested trough members, the or each pair comprising an inner trough member and an outer trough member associated with the diaphragm and extending at least partially thereacross, the inner trough member and the outer trough member being nested so as to define a space therebetween, the inner trough member opening to the vapour collection chamber and having one or more first apertures along its length and the outer trough member communicating laterally on each side with the vapour redistribution chamber by means of one or more second apertures opening laterally of the outer trough member along a respective side thereof into the vapour redistribution chamber, the space between the inner trough member and the outer trough member providing a tortuous passageway for vapour from the vapour collection chamber to the vapour redistribution chamber through the at least one first aperture, through the space between the inner trough member and the outer trough member, and then trough the at least one second aperture to discharge laterally into the vapour redistribution chamber; and
   f) a quench gas conduit associated with the or each pair of trough members and being provided with one or more third apertures along its length arranged to discharge quench gas into the vapour flowing along the tortuous pathway, whereby the diaphragm prevents passage of vapour from the vapour collection chamber to the vapour redistribution chamber and whereby vapour passes from the vapour collection chamber to the vapour redistribution chamber through the tortuous passageway and is admixed with quench gas in passage through the tortuous passageway.

2. A reactor according to claim 1, wherein the reactor further comprises baffle means adjacent the diaphragm extending across the interior of the pressure vessel and having at least one breach through which the vaporous reaction mixture is constrained to pass.

3. A reactor according to claim 2, wherein the breach comprises one or more grills forming part of the baffle means.

4. A reactor according to claim 2, wherein there is provided in association with the breach a barrier means comprising a deflection surface outstanding from the plane of the baffle means.

5. A reactor according to claim 4, wherein the barrier means comprises upstanding wall means defining a plurality of penned enclosures arranged along the length of the breach.

6. A reactor according to claim 4, wherein the barrier means comprises a wall running along the length of the breach and standing out from the surface of the baffle means, the wall having a series of slots or apertures along its length to allow the passage of a vaporous reaction mixture therethrough.

7. A reactor according to claim 6, wherein two parallel walls are provided, wherein one wall is provided on one side of the breach and another wall is provided on the opposite side of the breach.

8. A reactor according to claim 7, wherein the slots or apertures in one wall are linearly offset with respect to the other parallel wall.

9. A reactor according to claim 4, wherein the barrier means comprises a series of interleaved fingers outstanding from the plane of the baffle means.

10. A reactor according to claim 1, wherein the heterogeneous catalyst is a methanol synthesis catalyst.

11. A reactor according to claim 10, wherein the catalyst is a copper-containing catalyst.

12. A reactor according to claim 1, wherein the heterogeneous catalyst is an ammonia synthesis catalyst.

13. A reactor according to claim 12, wherein the ammonia synthesis catalyst is selected from Fe impregnated with at least one non-reducible oxide of a metal selected from K, Ca, Al, Be, Ce, Si and mixtures of two or more thereof.

14. A reactor according to claim 1, wherein the or each said quench gas conduit segments or segment the diaphragm in a symmetrical arrangement.

15. A reactor according to claim 1, wherein the inner and outer trough members are arcuate in section.

16. A reactor according to claim 1, wherein the second apertures are arranged in two sets each of one or more rows, one set being arranged to discharge vapour laterally to the vapour redistribution chamber on one side of the outer trough member and the other set being arranged to discharge vapour laterally to the distribution chamber on the other side of the outer trough member.

17. A reactor according to claim 16, wherein the two sets of second apertures are symmetrically positioned with respect to the axes of the outer trough member and of the quench gas conduit.

18. A reactor according to claim 1, wherein the quench gas conduit or conduits of one diaphragm is or are radially offset about the axis of the reactor with respect to the corresponding quench gas conduit or conduits of at least one other diaphragm within the pressure vessel.

19. A reactor according to claim 18, wherein the quench gas conduit or conduits of one diaphragm is or are radially offset about the axis of the reactor with respect to the quench gas conduit or conduits of at least one other diaphragm by an angle of between 20° and 90°.

20. A reactor according to claim 19, wherein the angle of radial offset is 90°.

21. A reactor according to claim 1, wherein the quench gas conduit associated with the or each respective pair of trough members is mounted at least partially within the inner trough member of the pair.

22. A continuous process for conducting an exothermic vapour phase reaction, which process comprises:
   a) supplying to a pressure vessel via inlet means therefor a gaseous reactant or reactants;

b) maintaining in the pressure vessel temperature and pressure conditions effective for production of the desired product by means of the exothermic vapour phase reaction;

c) allowing the gaseous reactant or reactants to flow in turn through a plurality of beds of a heterogeneous catalyst effective for catalysts of the exothermic vapour phase reaction, each bed being supported within the pressure vessel by a respective support means;

d) collecting vaporous reaction mixture exiting a first bed of each successive pair of beds in a vapour collection chamber disposed adjacent an exit end of said first bed of the pair, the vapour collection chamber being separated from a corresponding downstream vapour redistribution chamber disposed adjacent an inlet end of the other bed of the pair and arranged for redistributing vapour over the inlet end of said other bed of the respective pair by a diaphragm extending across the interior of the pressure vessel, the diaphragm preventing the flow of vapour from the vapour collection chamber to the vapour redistribution chamber;

e) allowing vaporous reaction mixture to pass from the vapour collection chamber to the vapour redistribution chamber by means of a tortuous passageway formed by at least one pair of nested trough members comprising an inner trough member and an outer trough member associated with and extending at least partially across the diaphragm, the inner trough member opening to the vapour collection chamber and having one or more first apertures along the length of the inner trough member and the outer trough member communicating laterally on each side with the vapour redistribution chamber by means of one or more second apertures opening laterally of the outer trough member into the vapour redistribution chamber along a respective side thereof, the space between the inner trough member and the outer trough member providing said tortuous passageway for vapour from the vapour collection chamber to the vapour redistribution chamber through the at least one first aperture, through the space between the inner trough member and the outer trough member, and then through the at least one second aperture to discharge laterally into the vapour redistribution chamber;

f) supplying quench gas to the vaporous reaction mixture passing through the diaphragm by means of a quench gas conduit associated with each pair of inner and outer trough members, the quench gas conduit being provided with one or more third apertures along its length arranged to discharge quench gas into the vapour flowing along the tortuous pathway; and g) recovering from the pressure vessel via outlet means provided downstream from the final catalyst bed a vaporous product stream containing said product, whereby the diaphragm prevents passage of vapour from the vapour collection chamber to the vapour redistribution chamber and whereby vapour passes from the vapour collection chamber to the vapour redistribution chamber through the tortuous passageway and is admixed with quench gas in passage through the tortuous passageway.

23. A process according to claim 22 including providing adjacent the diaphragm a baffle means extending across the interior of the pressure vessel and having at least one breach through which the vaporous reaction mixture is constrained to pass.

* * * * *